(12) United States Patent
She et al.

(10) Patent No.: US 7,531,627 B2
(45) Date of Patent: May 12, 2009

(54) PROTEIN ACA1 OF ANTRODIA CAMPHORATA

(75) Inventors: Fuu She, Taipei (TW); Kuang-Yang Hsieh, Taipei (TW); Po-Jung Chien, No. 140, Sec. 4th, Kee-Long Rd., Taipei City (TW) 106; Chiao-Yin Tsao, Taipei County (TW); Kah-Lock Chin, Melaka (MY)

(73) Assignee: Po-Jung Chien, Taipei (TW)

( * ) Notice: Subject to any disclaimer, the term of this patent is extended or adjusted under 35 U.S.C. 154(b) by 505 days.

(21) Appl. No.: 11/015,078

(22) Filed: Dec. 18, 2004

(65) Prior Publication Data

US 2005/0164931 A1    Jul. 28, 2005

(30) Foreign Application Priority Data

Dec. 19, 2003   (TW) .............................. 92136095 A

(51) Int. Cl.
  *C07K 1/00*   (2006.01)
  *C07K 14/00*  (2006.01)
  *C07K 17/00*  (2006.01)
(52) U.S. Cl. ..................................... 530/350
(58) Field of Classification Search .................. 530/350
  See application file for complete search history.

(56) References Cited

OTHER PUBLICATIONS

Gerhold et al 1996 BioEssays, vol. 18, No. 12, pp. 973-981.*
Bowie et al Science, 1990, 247:1306-1310.*
Wen-Huei Lin et al, "Dimerization of the N-terminal Amphipathicα-Helix Domain of . . . ", The Journal of Biological Chemistry, vol. 272, No. 32, 20044-20048 (Aug. 8, 1997), by Amerian Society for Biochemistry & Molecular Biology, Inc., in U.S.A.
Palasingam Paaventhan et al, "A 1.7 Å Structure of Fve, a Member of the New Fungal Immunomodulatory Protein Family", J. Mol. Biol. vol. 332, 461-470 (2003), by Elsevier Ltd.
Hao-Chi Hsu et al, "Fip-vvo, a new fungal immunomodulatory protein isolated from *Volvariella volvacea*", Biochem. J., vol. 323, 557-565 (1997), in Great Britain.
Sheng-Yuan Wang et al, "The anti-tumor effect of *Ganoderma lucidum* is mediated by cytokines released from activated macrophages and T lymphocytes", Int. J. Cander, vol. 70. 699-705 (1997), Wiley-Liss, Inc.
K.-Y. Hsieh et al, "Oral administration of an edible-mushroom-derived protein inhibits the development of food-allergic reactions in mice", Clin. Exp. Allergy, vol. 33, 1-8 (2003), Blackwell Publishing Ltd.

* cited by examiner

*Primary Examiner*—Mark Navarro
*Assistant Examiner*—Nina A Archie
(74) *Attorney, Agent, or Firm*—Pai Patent & Trademark Law Firm; Chao-Chang David Pai; Jeffrey R. Ouimet

(57) ABSTRACT

A new protein, named ACA1, has been isolated and purified from the medical fungi *Antrodia camphorata* using the technique of anion-exchange chromatography. ACA1, a glycoprotein with a molecular mass of 29 kDa, has a pI value of pH 5.3 and contains 118 amino acids in its peptide moiety. In addition, ACA1 contains methionine, half-cystine and histidine residues, which are not existent in FIP-fve and Ling Zhi-8. ACA1 is not able to agglutinate red blood cells from human and mouse. Moreover, ACA1 possesses immunomodulatory activities, which are demonstrated by their stimulatory activity toward RAW 264.7 macrophages and mouse splenocytes. ACA1 can directly enhance the production of tumor necrosis factor-alpha and nitric oxide by RAW 264.7 macrophages, and induce cell proliferation and interferon-gamma secretion by mouse splenocytes.

3 Claims, 12 Drawing Sheets

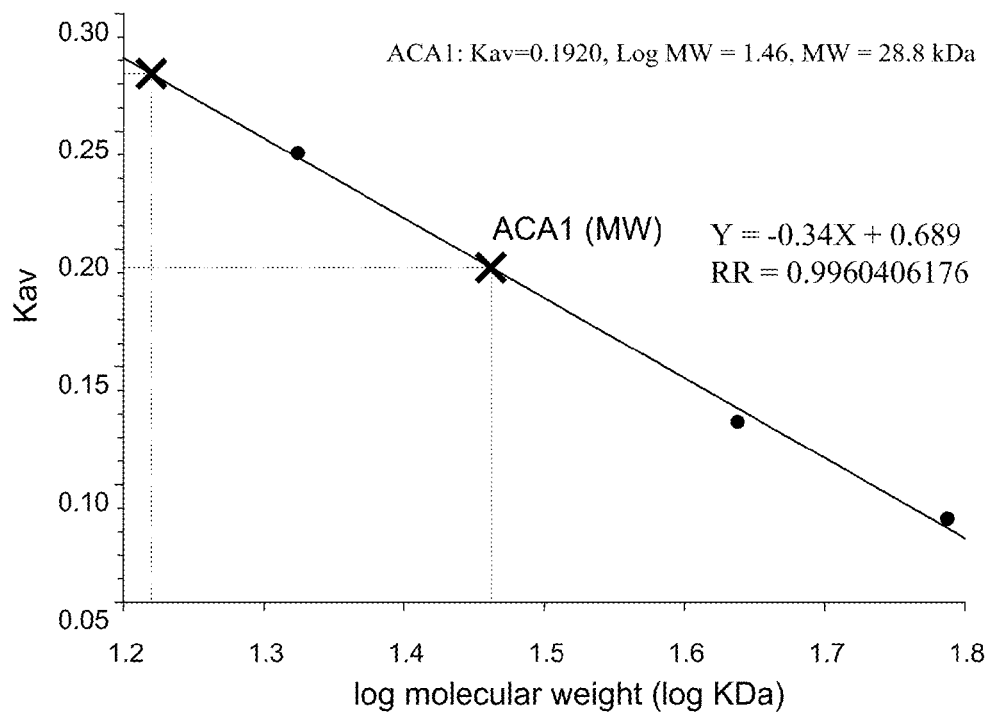
FIG.7
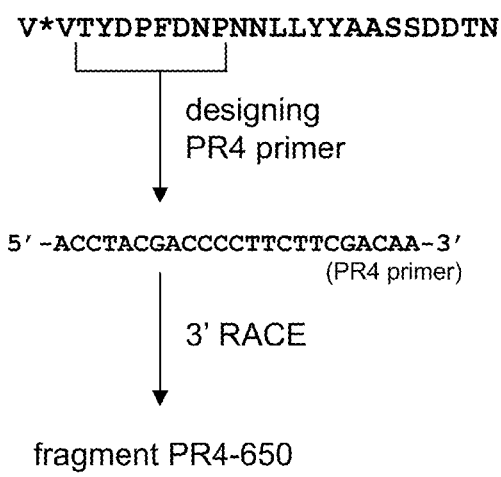
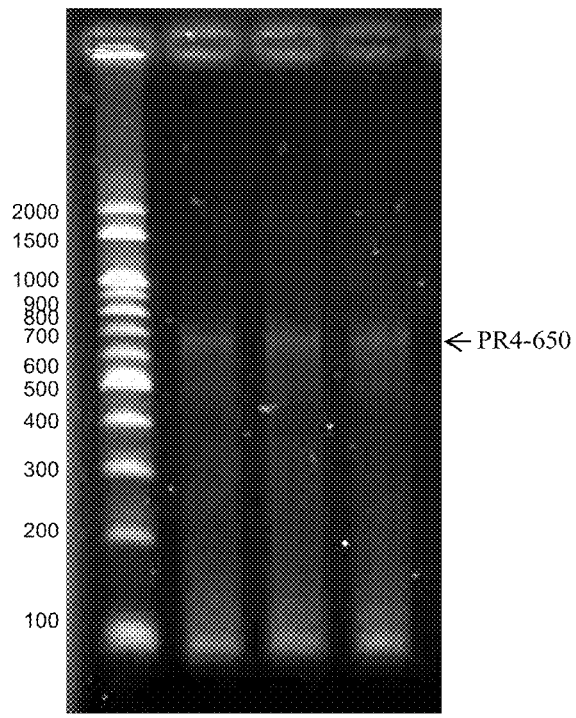
FIG.9

PR4-650

```
1     ACC TAC GAC CCC TTC TTC GAC AAC CCA AAC AAC TCT CTC AGC TAC    45
1      T   Y   D   P   F   F   D   N   P   N   N   S   L   S   Y    15

46    GTC GCT TGC TCG GAT GGT ACC AAT GGT CTT CTC ACC AAA GGG TAT    90
16     V   A   C   S   D   G   T   N   G   L   L   T   K   G   Y    30

91    ACC ACC TTG GGC TCC CTC CCT GAT TTC CCT TAC ATT GGA GGC GCA   135
31     T   T   L   G   S   L   P   D   F   P   Y   I   G   G   A    45

136   TAT GCC ATC GCA GGA TGG AAT TCC CCG AGC TGT GGC ACA TGT TGG   180
46     Y   A   I   A   G   W   N   S   P   S   C   G   T   C   W    60

181   GAG CTA ACA TAC AAC AAC GTC AGC ATC AAC ATA TTG GGG ATC GAC   225
61     E   L   T   Y   N   N   V   S   I   N   I   L   G   I   D    75

226   ACA GCT GCG GGC TTC AAC ATT GCA CTT ACG GCT ATG AAC GTA CTC   270
76     T   A   A   G   F   N   I   A   L   T   A   M   N   V   L    90

271   ACC AAT AAC GCG GCC GTA GAT CTG GGG GAG GTT GAT GCA ACG GCA   315
91     T   N   N   A   A   V   D   L   G   E   V   D   A   T   A   105

316   ATA CAG GTC GAC TCG TCC GTG TGC GGG CTG TAA AGA TAT GTA AAA   360
106    I   Q   V   D   S   S   V   C   G   L   *   R   Y   V   K   120

361   CAG CTG GAA ATT TGT GGA CGA TGT CAT ATG TCA TCA TTT TGG ACT   405
121    Q   L   E   I   C   G   R   C   H   M   S   S   F   W   T   135

406   CGT GGC ATA GTC GAA ACT GAT GCC TAG TGT GTC ATT AAA GTC TCT   450
136    R   G   I   V   E   T   D   A   *   C   V   I   K   V   S   150

451   TGT TAC CAC CAA ACA ATG CTC GAC GTG AGA TCG TGG GGA GAA TGT   495
151    C   Y   H   Q   T   M   L   D   V   R   S   W   G   E   C   165

496   TTG ATT GTT TAG GAG TAT CGA ATT GGG ACA AAT TTA AAC ATA AAA   540
166    L   I   V   *   E   Y   R   I   G   T   N   L   N   I   K   180

541   AAA AAA AAA AAA AAA GAA AAA AAA AAC AAA AAA AAA AAA AAA AAA   585
181    K   K   K   K   K   E   K   K   N   K   K   K   K   K   K   195

586   AAA AAA AAG TAC TCT GCG TTG ATA CCT CTG CTT   618
196    K   K   K   Y   S   A   L   I   P   L   L
```

N-terminal AA sequence of ACA1: V*VTYDPFFDNPPNNLLYYAASSDDTN translated AA sequence of pr4-650: TYDPFFDNP-NNSLSYVACSDGTNGLLTKGY....

PR4 location

| | | | | | | | | | | | | | | | | |
|---|---|---|---|---|---|---|---|---|---|---|---|---|---|---|---|---|
| 2 | GAT | TCT | ATG | CTA | TAC | CGA | GCA | GCA | CCT | ACA | GCG | CGA | CCA | ACT | GCC | 46 |
| 1 | D | S | M | L | Y | R | A | A | P | T | A | R | P | T | A | 15 |
| 47 | TTC | CGT | TCC | ACA | ATA | GCC | ATG | AAG | GTC | GCT | GTC | GCC | CTC | AGT | GCT | 91 |
| 16 | F | R | S | T | I | A | M | K | V | A | V | A | L | S | A | 30 |
| 92 | CTC | TTC | CTC | CTT | CCC | TCC | GCT | CTC | GGT | GTA | AAC | GTG | ACC | TAT | GAC | 136 |
| 31 | L | F | L | L | P | S | A | L | G | V | N | V | T | Y | D | 45 |
| 137 | CCT | TTT | TTC | GAC | AAC | CCA | AAC | AAC | TCT | CTC | AGC | TAC | GTC | GCT | TGC | 181 |
| 46 | P | F | F | D | N | P | N | N | S | L | S | Y | V | A | C | 60 |
| 182 | TCG | GAT | GGT | ACC | AAT | GGT | CTT | CTC | ACC | AAA | GGG | TAT | ACC | ACC | TTG | 226 |
| 61 | S | D | G | T | N | G | L | L | T | K | G | Y | T | T | L | 75 |
| 227 | GGC | TCC | CTC | CCT | GAT | TTC | CCT | TAC | ATT | GGA | GGC | GCA | TAT | GCC | ATC | 271 |
| 76 | G | S | L | P | D | F | P | Y | I | G | G | A | Y | A | I | 90 |
| 272 | GCA | GGA | TGG | AAT | TCC | CCG | AGC | TGT | GGC | ACA | TGT | TGG | GAG | CTA | ACA | 316 |
| 91 | A | G | W | N | S | P | S | C | G | T | C | W | E | L | T | 105 |
| 317 | TAC | AAC | AAC | GTC | AGC | ATC | AAC | ATA | TTG | GGG | ATC | GAC | ACA | GCT | GCG | 361 |
| 106 | Y | N | N | V | S | I | N | I | L | G | I | D | T | A | A | 120 |
| 362 | GGC | TTC | AAC | ATT | GCA | CTT | ACG | GCT | ATG | AAC | GTA | CTC | ACC | AAT | AAC | 406 |
| 121 | G | F | N | I | A | L | T | A | M | N | V | L | T | N | N | 135 |
| 407 | GCG | GCC | GTA | GAT | CTG | GGG | GAG | GTT | GAT | GCA | GCG | GCA | ATA | CAG | GTC | 451 |
| 136 | A | A | V | D | L | G | E | V | D | A | A | A | I | Q | V | 150 |
| 452 | GAC | TCG | TCC | GTG | TGC | GGG | CTG | TAA | AGA | TAT | GTA | AAA | CAG | CTG | GAA | 496 |
| 151 | D | S | S | V | C | G | L | * | R | Y | V | K | Q | L | E | 165 |
| 497 | ATT | TGT | GGA | CGA | TGT | CAT | ATG | TCA | TCA | TTT | TGG | ACT | CGT | GGC | ATA | 541 |
| 166 | I | C | G | R | C | H | M | S | S | F | W | T | R | G | I | 180 |
| 542 | GTT | GAA | ACT | GAT | GCC | TAG | TGT | GTC | ATT | AAA | GTC | TCT | TGT | TAC | CAC | 586 |
| 181 | V | E | T | D | A | * | C | V | I | K | V | S | C | Y | H | 195 |
| 587 | CAA | ACA | ATG | CTC | GAC | GTG | AGA | TCG | TGG | GGA | GAA | TGT | TTG | ATT | GTT | 631 |
| 196 | Q | T | M | L | D | V | R | S | W | G | E | C | L | I | V | 210 |
| 632 | TAG | GAG | TAT | CGA | ATT | GGG | | 649 | | | | | | | | |
| 211 | * | E | Y | R | I | G | | 216 | | | | | | | | |

```
V*VTYDPFFDNPPNNLLYYAASSDDTN
  ||||||||||  ||  |  |||  ||  ||
  ||||||||||  ||  |  |||  ||  ||
  ||||||||||  ||  |  |||  ||  ||
  ||||||||||  ||  |  |||  ||  ||
   TYDPFFDNP-NNSLSYVACSDGTNGLLTKGY...
  ||||||||||||||||||||||||||||||
  ||||||||||||||||||||||||||||||
  ||||||||||||||||||||||||||||||
..LGVNVTYDPFFDNP-NNSLSYVACSDGTNGLLTKGY...
```

N-terminal AA sequence of ACA1 (Edman reaction):

translated AA sequence of pr4-650:

translated AA sequence of pr14-700:

FIG.12

ACA1 sequence

```
2     GAT TCT ATG CTA TAC CGA GCA GCA CCT ACA GCG CGA CCA ACT GCC   46
1      D   S   M   L   Y   R   A   A   P   T   A   R   P   T   A   15

47    TTC CGT TCC ACA ATA GCC ATG AAG GTC GCT GTC GCC CTC AGT GCT   91
16     F   R   S   T   I   A   M   K   V   A   V   A   L   S   A   30

92    CTC TTC CTC CTT CCC TCC GCT CTC GGT GTT AAC GTG ACC TAT GAC   136
31     L   F   L   L   P   S   A   L   G   V   N   V   T   Y   D   45

137   CCT TTT TTT GAC AAC CCA AAC AAC TCT CTC AGC TAC GTC GCT TGC   181
46     P   F   F   D   N   P   N   N   S   L   S   Y   V   A   C   60

182   TCG GAT GGT ACC AAT GGT CTT CTC ACC AAA GGG TAT ACC ACC TTG   226
61     S   D   G   T   N   G   L   L   T   K   G   Y   T   T   L   75

227   GGC TCC CTC CCT GAT TTC CCT TAC ATT GGA GGC GCA TAT GCC ATC   271
76     G   S   L   P   D   F   P   Y   I   G   G   A   Y   A   I   90

272   GCA GGA TGG AAT TCC CCG AGC TGT GGC ACA TGT TGG GAG CTA ACA   316
91     A   G   W   N   S   P   S   C   G   T   C   W   E   L   T   105

317   TAC AAC AAC GTC AGC ATC AAC ATA TTG GGG ATC GAC ACA GCT GCG   361
106    Y   N   N   V   S   I   N   I   L   G   I   D   T   A   A   120

362   GGC TTC AAC ATT GCA CTT ACG GCT ATG AAC GTA CTC ACC AAT AAC   406
121    G   F   N   I   A   L   T   A   M   N   V   L   T   N   N   135

407   GCG GCC GTA GAT CTG GGG GAG GTT GAT GCA GCG GCA ATA CAG GTC   451
136    A   A   V   D   L   G   E   V   D   A   A   A   I   Q   V   150

452   GAC TCG TCC GTG TGC GGG CTG TAA AGA TAT GTA AAA CAG CTG GAA   496
151    D   S   S   V   C   G   L   *   R   Y   V   K   Q   L   E   165

497   ATT TGT GGA CGA TGT CAT ATG TCA TCA TTT TGG ACT CGT GGC ATA   541
166    I   C   G   R   C   H   M   S   S   F   W   T   R   G   I   180

542   GTT GAA ACT GAT GCC TAG TGT GTC ATT AAA GTC TCT TGT TAC CAC   586
181    V   E   T   D   A   *   C   V   I   K   V   S   C   Y   H   195

587   CAA ACA ATG CTC GAC GTG AGA TCG TGG GGA GAA TGT TTG ATT GTT   631
196    Q   T   M   L   D   V   R   S   W   G   E   C   L   I   V   210

632   TAG GAG TAT CGA ATT GGG ACA AAT TTA AAC ATA AAA AAA AAA AAA   676
211    *   E   Y   R   I   G   T   N   L   N   I   K   K   K   K   225

677   AAA AAA GAA AAA AAA AAC AAA AAA AAA AAA AAA AAA AAA AAA AAG   721
226    K   K   E   K   K   N   K   K   K   K   K   K   K   K   K   240

722   TAC TCT GCG TTG ATA CCT CTG CTT     745
241    Y   S   A   L   I   P   L   L
```

(ACA1 encoding from 119 b.p. to 472 b.p.)

FIG.13

PROTEIN ACA1 OF ANTRODIA CAMPHORATA

BACKGROUND OF THE INVENTION

1. Field of the Invention

The present invention relates to a protein, named ACA1, purified from *Antrodia camphorata*, and more particularly to the amino acid sequence of ACA1 and its immunomodulatory activity, as demonstrated by its stimulatory activity toward RAW 264.7 macrophages and mouse splenocytes.

2. Description of the Related Art

*Antrodia camphorata* is a Taiwan specific mushroom having a special regional value. Although it has been existing in Taiwan for a long time, its first research report was published only as recently as in 1990. *Antrodia camphorata* is classified as Mycota, Basidiomycotina, Hymenomycetes, Phyllophorales, Polyporaceae, Antrodoa. The carpophores of *Antrodia camphorata* are perennial having a strong camphor tree aroma. Its shape is plate form or bell form, very different from the normal shape of *ganoderma*. The plate form, it cap is orange (yellow) color and full of gills, its floor plate has ivory color phellem, the *Antrodia camphorata* adhering to the inside wall of hollow wood of *cinnamomum comphora* grows by said phellem. The bell form, its carpophore (bell cap) also is orange (yellow) color and full of gills (4-5 gills/mm), and it has spores with bitter flavor. It is orange color in fresh, and then becomes dark orange color or brown color, bell body shows blackish green shell. To observe basidiospore by microscope, its shape is smooth, colorless, semi-bended pillar (3.5-5.0×1.5-2 μm).

There had been few reports on the physiological function of *Antrodia camphorata* before 2002, and there also lack the clinical and pharmaceutical evidences from science research. The well-known physiological functions of *Antrodia camphorata* are the curative effects passed on folk therapy, therefore in-depth research using scientic experiment is needed. On the physiological of fungus, *Antrodia camphorata* is the only mushroom that can metabolize a large number of bacteriostasis safrole of *cinnamomum comphora* and grows normally. It shows that *Antrodia camphorata* has a physiological metabolism function different from other mushrooms. The research, Cheng Yi Hua, 1994, indicates all of the triterpenoids elements of carpophore of *Antrodia camphorata* having 24(28)-en frame on its branch. It shows that the titerpenoids metabolism of *Antrodia camphorata* is very different from *ganoderma*, these branch frames can be the characteristic elements of *Antrodia camphorata*, the 30% methanol extract of *Antrodia camphorata* is more than 3% methanol extract of *ganoderma*, and *Antrodia camphorata* is bitterer than *Ganoderma*, because of *Antrodia camphorata* has more oxidated triterpenoids and sterol. Wang Bo-Che, food industry, 1998, 30: 1-36., indicates that *Antrodia camphorata* has valuable evaluation for detoxification of food poisoning ˋdiarrheaˋbellyache ˋvomit ˋpesticide. *Antrodia camphorata* is very well done in treating of hepato tumor and uterus tumor, settling spirit, and it is also a magic tool for protecting liver and dissolving drunkenness.

Recently, the academia has begun to actively research the functions and active ingredients of *Antrodia camphorata*. Tsai Yan Hui, 2002, master thesis of Department of Food Science, National Chung Hsing University, indicates that triterpene compound β which isolated from *Antrodia camphorata* carpophore has reducing acute liver damage induced by carbon tetrachloride in the rat liver functional experiments and reducing mouse's blood GPT value. Song, T. Y et al., 2002, Journal Agriculture Food Chemistry, 50: 3322-3327 and 2003, Journal Agriculture Food Chemistry, 51: 1571-1577, indicate that the ferment filtrate of *Antrodia camphorata* has highly ability to protect acute liver damage of rat induced by carbon tetrachloride. Chen Li Yan et al., 2002, in seminar and Chen Xin Yi, 2002, master thesis of China Medical School Institute of Nutrition, indicate adequate ferment filtrate of *Antrodia camphorata* mycelium has positive effect for liver physiological function, it can reduces liver fibrosis and denature, increases GSH content in liver and erythrocyte and the activity of antioxidate enzyme, decreases liver lipid peroxidation, and good for decreases body oxidation pressure. Yang Su We, 1991, master thesis of National Taiwan University Institute of Pharmacy, indicates after extract of *Antrodia camphorata* divide extracted with ethyl acetate and water, the activities of anticholine and antiserotonin of ethyl acetate level are the strongest, and have the curative effect certainly. Chen Jin Chu, 2001, in seminar, discloses the preliminary safe experiment of *Antrodia camphorata*, he detects that *Antrodia camphorata* mycelium has no toxicity for various cell and mouse, and it is need to systematicness and widespread study the immunity regulationsˋanti-tumors and other physiologival functions of *Antrodia camphorata*. Chen Quing Nong et al., 1999, in seminar, indicate the special aroma of *Antrodia camphorata* has the ability of antibiotic and antioxidation, and it can apply in aromatherapy, the results of appraise said aroma elements are perpene alcohols and ethyl hexadecanoate etc. Grape King Inc. performs study of the ability of antihepatitis B virus and immunity of *Antrodia camphorata*, it shows rude extract of *Antrodia camphorata* has stronger activity of antihepatitis B virus, and after concanavalin A (ConA) treats, the *Antrodia camphorata* mycelium can promotes lymphocyte proliferation and irritates spleen cell producing cytokine IL-2.

In mushroom increasing immunity way, Lee S. S. et al., 1995, Journal of Chinese Medicine, 6:1-12, indicate every extracts of mushroom can increase immune cell activity, and promote cytokine and interferon production. Chen W. C. et al., 1999, the American journal of Chinese medicine, indicate the extract of mushroom can restore the immunity of mouse which immunity decreasing after irradiation. Furthermore, Ding Huai Qian, 2000, Food industry, 32:28-42, indicates scholars had been study in activity of immune physiology of edible and medicinal using mushrooms, such as ganodermaˋcoridus ganodermaˋtremellaˋchinese caterpillar fungusˋhericium erinaceumˋpolyporusˋgolden mushroomˋmushroom and maitake mushroom, base on different kinds of mushroom, individual of them possesses some abilities of promoting lymphocyte proliferation, activating B cell and increasing serum antibody content, raising phagocytic ability of macrophage and nature killer cell, promoting reaction of SRBC and PFC, having inhibitions to resist immunity inhibitor such as cyclophosphamide, mercaptopurine, fluorouracil, and promoting ConA induced mouse spleen lymphocyte proliferation, isoform antigen irritating transformation of lymphocyte. Lieu C.W. et al., 1992, Anticancer Research, 12:1211-1215ˋSakagami MRS. et al., 1993, Anticancer Research, 13:671-675ˋWang H. et al., 2001, Biochemical and biophysical research communications, 275: 810-816 and 2002, Biochemical and biophysical research communications, 289: 750-755, organism activates immune system to kill cancer cell or inhibit tumor growing due to the extract of mushroom can activate various body immune cell ˋraises the phagocytic ability of macrophage and nature killer cellˋstimulates immune cell secreting various interferon and cytokines to inhibit tumor cell. Therefore, it is positive relation in the ability of anti-tumor of the extract of mushroom and the ability of promoting immunity of the extract of mushroom.

*Antrodia camphorata* is a Taiwan specific fungus, and has various physiology activities, but its activated elements are not clear before. The protein ACA1 from *Antrodia camphorata* mycelium was purified and its immunomodulatory activity disclosed in this invention.

BRIEF SUMMARY OF THE INVENTION

In this invention, a protein named ACA1 is extracted from *Antrodia camphorata* and purified using the technique of ion-exchange chromatography. The nucleic acid sequence of ACA1 using 3'-RACE cloning of the gene of ACA1. The ACA1 protein consists of 118 amino acid residues with a molecular mass of about 29 kDa.

The ACA1 of the present invention is useful because of its immunomodulatory activity in that it can activate RAW 264.7 macrophage and mouse spleen cell, enhance the production of TNF-alpha and nitric oxide by RAW 264.7 macrophages, and induce cell proliferation and IFN-gamma secretion by mouse splenocytes.

BRIEF DESCRIPTION OF THE DRAWINGS

The patent or application file contains at least one drawing executed in color. Copies of this patent or patent publication with color drawings will be provided by the Office upon request and payment of the necessary fee.

The features, aspects, and advantages of the present invention will be fully described in the section of Detailed Description of the Invention with reference to the accompanying drawings as follows:

FIG. 7 shows the molecular mass of ACA1 as analyzed by size exclusion.

FIG. 9 shows the electrophoresis result of PR4-650 fragment cloned by 3' RACE.

FIG. 10 shows the nucleic acid sequence and amino acid sequence of the PR4-650 gene fragment.

FIG. 12 shows the nucleic acid sequence and amino acid sequence of the PR14-700 gene fragment.

FIG. 13 shows the nucleic acid sequence and amino acid sequence of ACA1 gene.

DETAILED DESCRIPTION OF THE INVENTION

The present invention relates to purification of a protein, named ACA1, by the technique of ion-exchange chromatography, and to obtaining the nucleic acid sequence of ACA1 using 3'-RACE cloning of the gene of ACA1. The ACA1 of the present invention is useful because it possesses the immunomodulatory activity: it can activate RAW 264.7 macrophage and mouse spleen cell, enhance the production of TNF-alpha and nitric oxide by RAW 264.7 macrophages, and induce cell proliferation and IFN-gamma secretion by mouse splenocytes.

1. Purification of the Protein ACA1 of *Antrodia camphorata*

Figure 1:
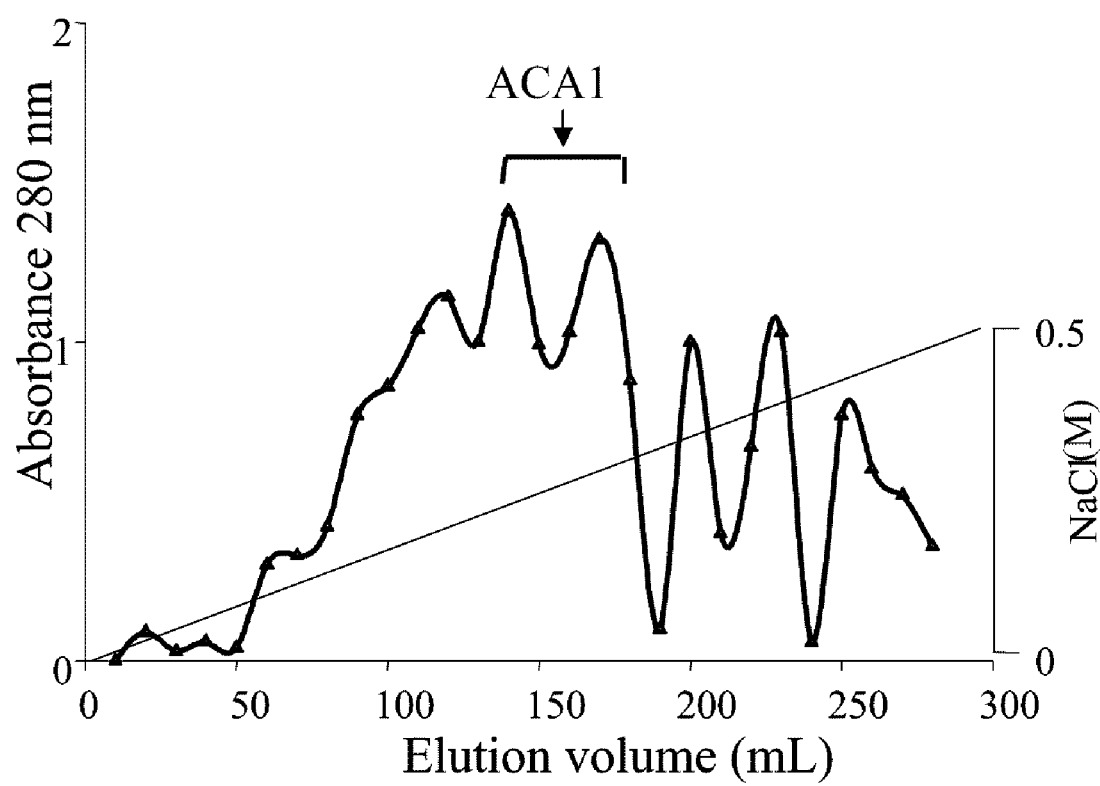
FIG. 1 shows the purification of ACA1 via DE-52 column.
Figure 2:
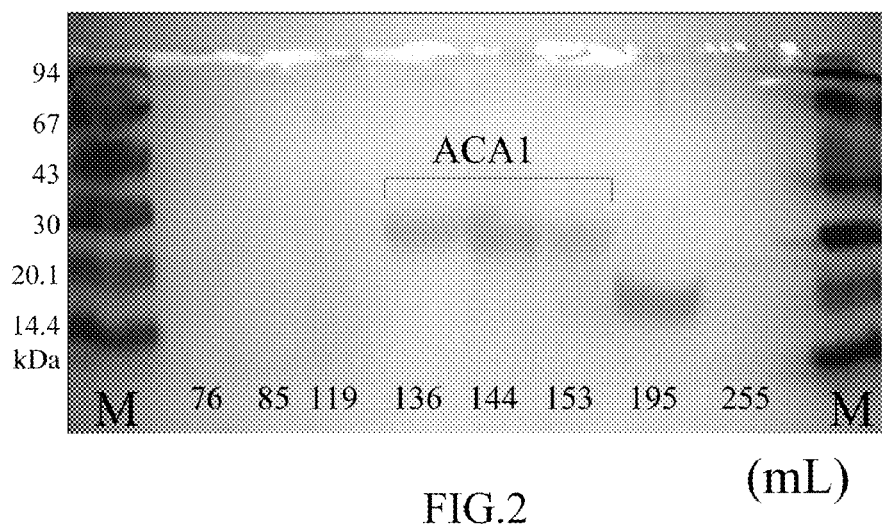
FIG. 2 shows the result of protein electrophoresis of ACA1 after purification in DE-52 column.

(a) To filtrate 10 L ferment liquid of *Antrodia camphorata* using 110 mm filter for gets about 1 kg wet weight mycelium, after it isolated, the rude extract deposits protein by saturated solid ammonium sulphate, when said deposited protein dialysis completely, said protein has put it to pass through DE-52 anion-exchange chromatography to isolate the protein of *Antrodia camphorata*, using 280 nm detects it absorbance to get several absorption peaks such as FIG. 1. FIG. 2 shows the result of SDS-PAGE protein electrophoresis of ACA1.

Figure 3:
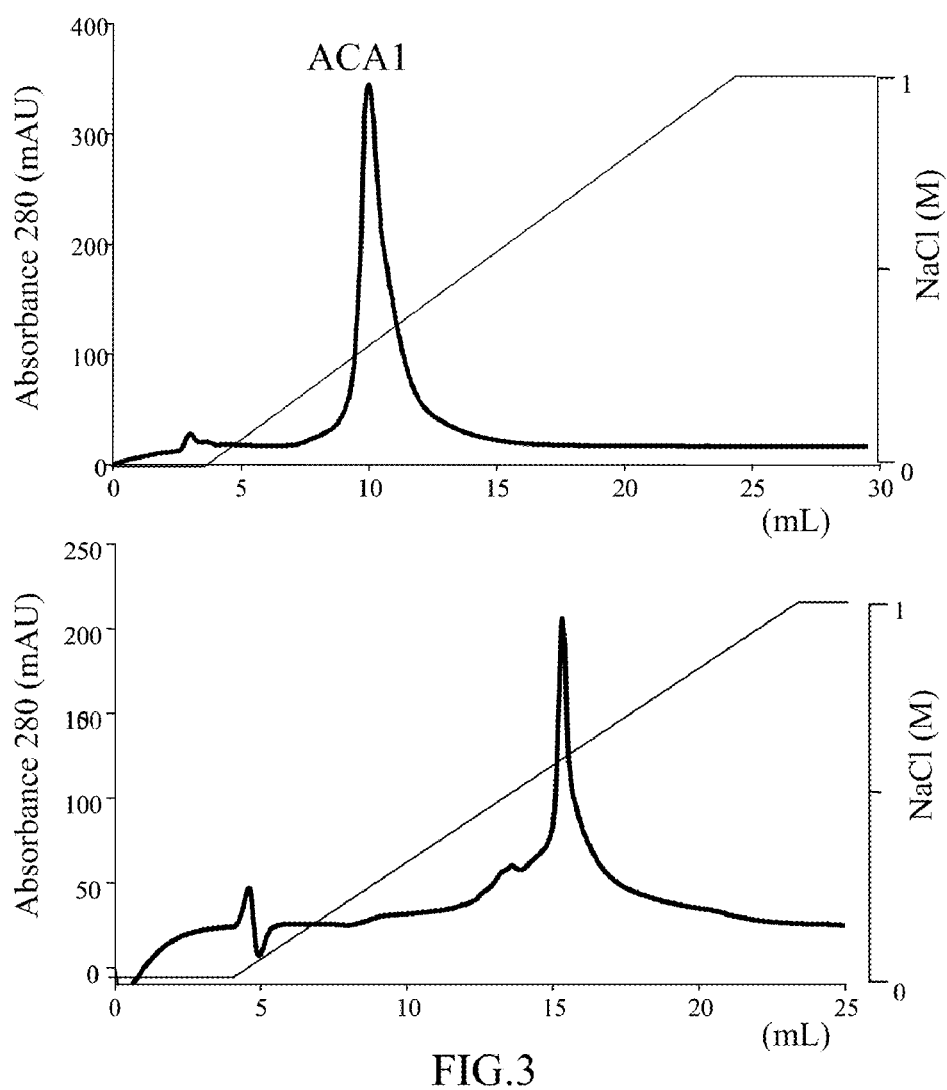
FIG. 3 shows the purification of ACA1 via FPLC Mono Q column.

(b) According to the characteristic of anion adsorption of ACA1, the protein is purified by the Mono-Q column FPLC and the chromatography atlas shows a single peak as in FIG. 3. The protein is further purified to obtain protein ACA1 of *Antrodia camphorata*. Every liter of the ferment liquid of *Antrodia camphorata* has 2.5 mg ACA1.

Figure 4:
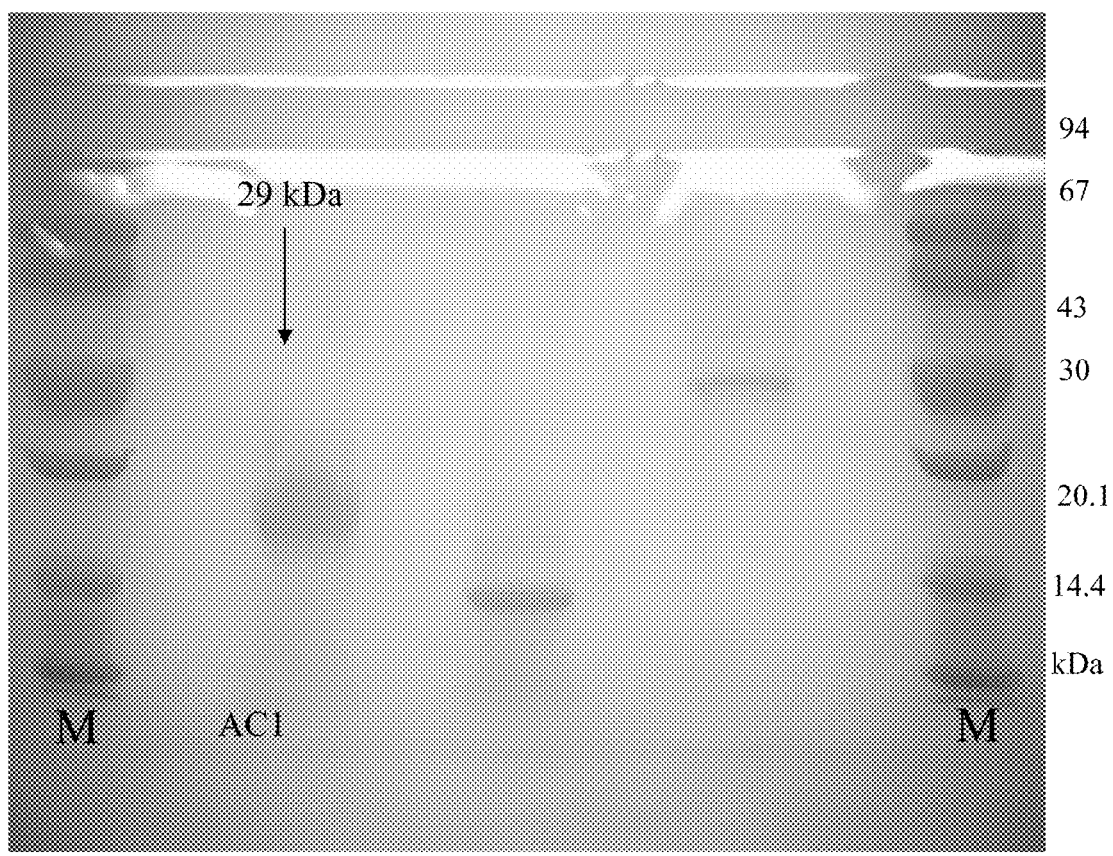
FIG. 4 shows the molecular mass of ACA1 as analyzed by SDS/PAGE.
Figure 5:
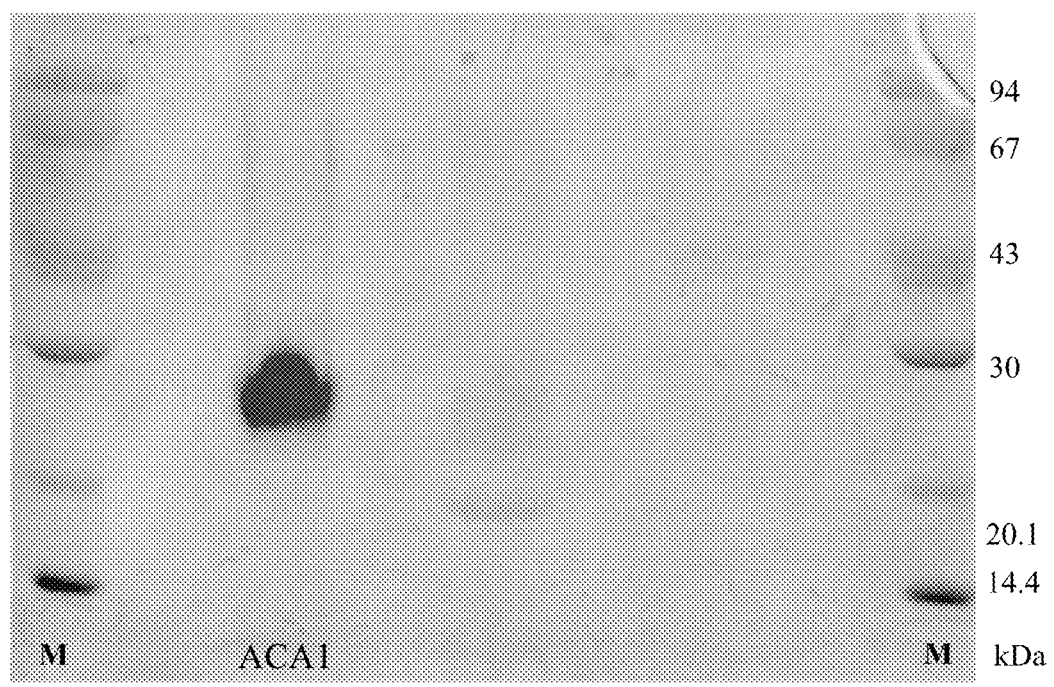
FIG. 5 shows the glycoprotein staining of ACA1.

(c) As shown in FIG. 4, the molecular mass of the protein ACA1 of *Antrodia camphorata* is 29 kDa from SDS/PAGE analysis. The electrophoresis film of SDS/PAGE performs the glycoprotein stain, as shown in FIG. 5, ACA1 has reaction with Schiff reagent, and display purple band, therefore said ACA1 is a glycoprotein.

Figure 6:
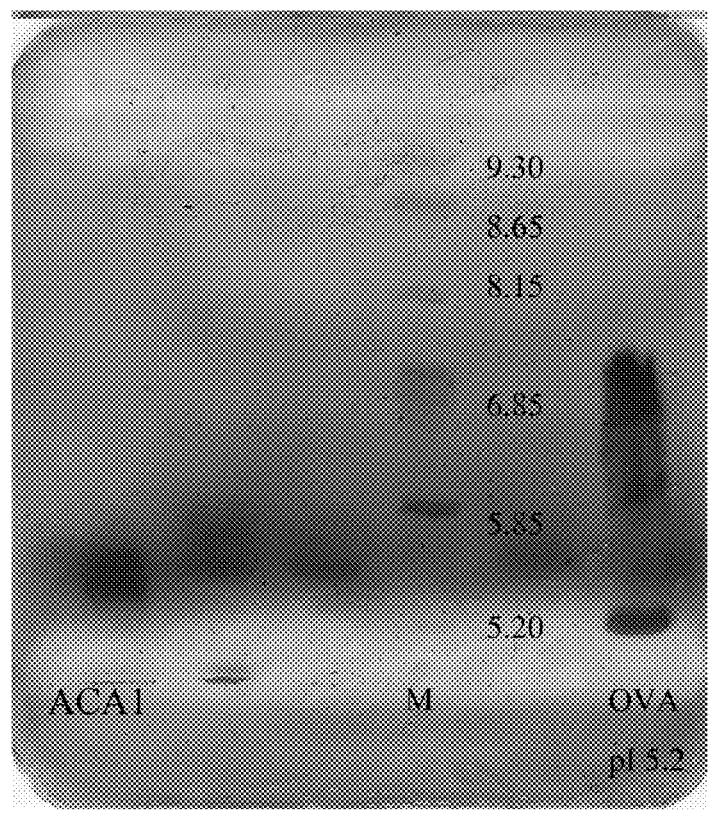
FIG. 6 shows the pI analysis of ACA1.

(d) To detect the isoelectric point (pI) of purified ACA1 via ion focusing electrophoresis (IEF), as shown in FIG. 6. In contrast with standard (Pharmacia pI calibration kit, IEF 3-9) and positive control (OVA: pI5.2), and after analyzed by cell molecule photography, they get the pI value of ACA1 of 5.3.

(e) Using the theorem of size exclusion, separate ACA1 from standard protein which held up in column by gel filtration to determine molecular mass. The result shows that the molecular mass of ACA1 is 28.8 kDa (FIG. 7).

Figure 8:
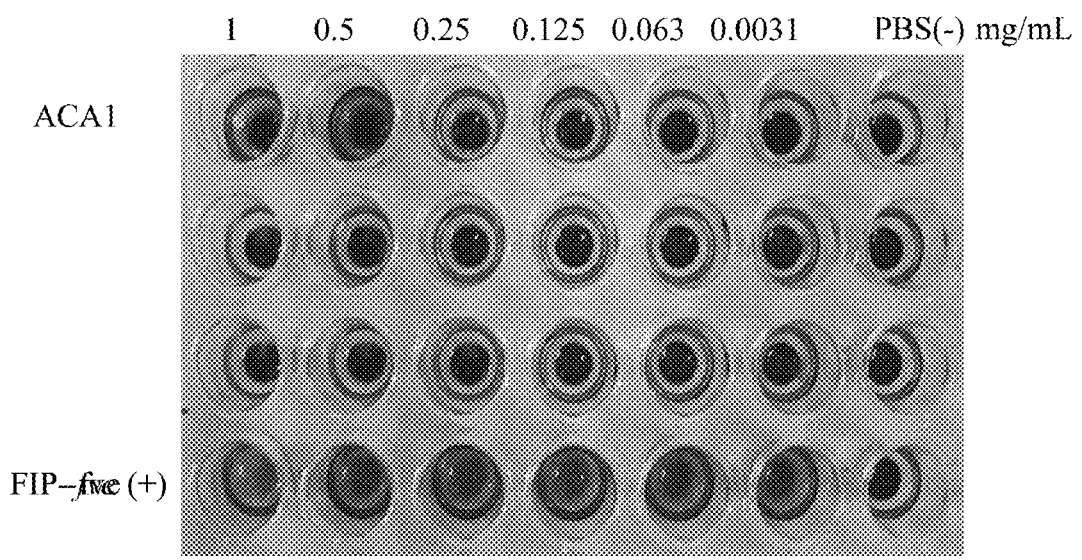
FIG. 8 shows the hemagglutination activity of ACA1.

(f) To perform the hemagglutination activity test for said ACA1 protein, said protein mixing with Balb/C and the situation of hemagglutination show in FIG. 8. In FIG. 8, comparing purified ACA1 in original concentration and diluted concentration ,0.5, 0.25, 0.125, 0.063, 0.0031 mg/ml with FIP-fve (which is a immune regulate protein having significant hemagglutination activity), it shows said protein have no hemagglutination activity.

2. ACA1 Cloning and its Amino Acid Sequence (a) After electrophoresis from SDS-PAGE, ACA1 is transferred to PVDF to perform the N-terminal amino acid sequence analysis for ACA1. The result shows that the N-terminal amino acid sequence of ACA1 is VNVTYDPFFDNP-PNNLLYYAASSDDTN.

(b) In the ACA1 gene cloning, the mycelium of *Antrodia camphorata* was cultivated and its total RNA was extracted first, and then the complementary DNA (cDNA) of *Antrodia camphorata* mRNA was produced by reverse transcription to be used as the template for cloning. The 3'RACE technique was used to amplify ACA1 gene by PCR. The primers of 3'-RACE reaction were designed from inferring possible nucleic acid codon from the N-terminal amino acid sequence of ACA1.

(c) Possible mapping primers for ACA1 were designed from the N-terminal amino acid sequence of ACA1, and the cloning was done by the 3' RACE techniques. The primer ACCTACGACCCCTTCTTCGACAA (5' to 3') was designed from the third amino acid to the ninth amino acid of ACA1 of the N terminal. Following 3'-RACE reaction, a nuleic acid fragment of 650 base pairs was obtained according to electrophoresis (FIG. 9).

(d) The nucleic acid of 650 base pairs obtained from 3'-RACE was cloned by TA cloning. After it is introduced to pGEMT vector, said the nucleic acid fragment of 650 base pairs was analyzed and the PR4-650 sequence was obtained (see FIG. 10). Then the PR4-650 sequence was translated into amino acid sequence. Comparing the sequence with ACA1 amino acid sequence shows that 19 amino acids of the 24 amino acids in the sequence obtained from Edman reaction are the same as those in the amino acid sequence translated from PR4-650 sequence. With a homogeneity as high as 79.2% (see FIG. 10) the two are very similar to each other.

Figure 11:
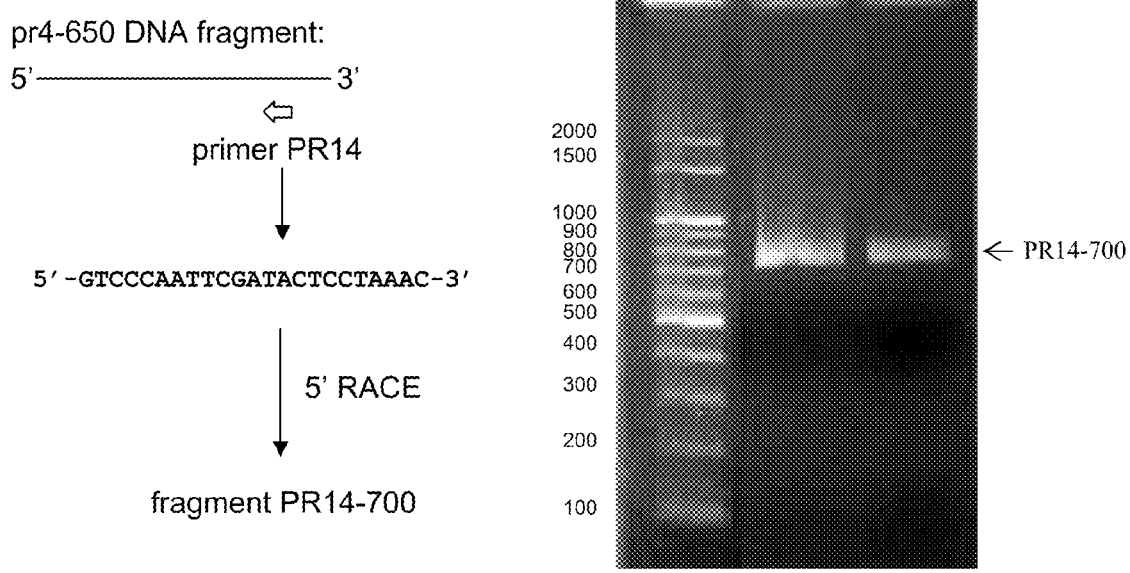
FIG. 11 shows the electrophoresis result of PR14-700 fragment cloned by 5' RACE.

(e) The primer GTCCCAATTCGATACTCCTAAAC of PR14 was designed by using PR4-650 sequence. The nucleic acid sequence before the third amino acid of ACA1 was cloned by 5'-RACE. The result was a fragment of the 700 base pairs, as shown in FIG. 11.

(f) The nucleic acid fragment of 700 base pairs obtained from 5'-RACE was cloned by TA cloning. After it is introduced to pGEMT vector, it analyzes said nucleic acid fragment of 700 base pairs was analyzed and the PR14-700 sequence was obtained (see FIG. 12). Then PR14-700 sequence was translated into amino acid sequence. Comparing the sequence with ACA1 amino acid sequence shows that both the first and the third cloned amino acids are V, as in the same as sequence. It is found from cloning that the second cloned amino acid (FIG. 12).

(g) To compare nucleic acid of PR4-650 with nucleic acid of PR14-700, and confirm by nested PCR for acquire the nucleic acid sequence and amino acid sequence of ACA1, as shown in FIG. 13. The expression set is beginning at the $119^{th}$ nucleic acid to the $472^{th}$ nucleic acid or the $40^{th}$ amino acid to $157^{th}$ amino acid.

To compare ACA1 nucleic acid sequence with nucleic acid of PR4-650 and nucleic acid of PR14-700, the *Antrodia camphorata* protein, ACA1 has the amino acid sequence or has the amino acid sequence more than 90% similarity as the amino acid sequence of FIG.13

Figure 14:
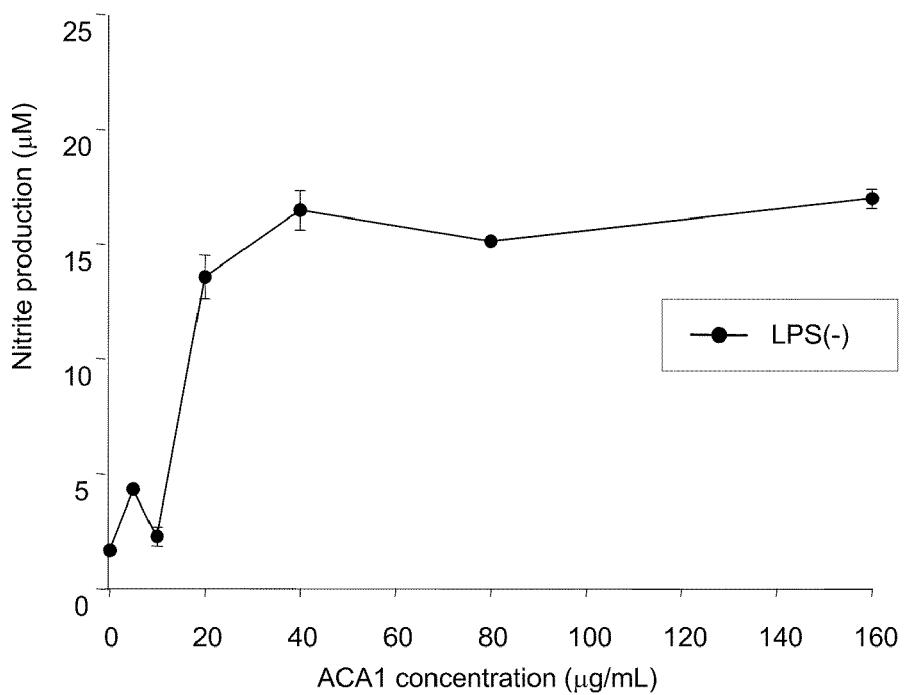
FIG. 14 shows the effect of ACA1 in activating RAW 264.7 macrophage to produce NO.

4. ACA1 activates RAW264.7 macrophage (a) After ACA1 and RAW264.7 macrophage were co-cultivated for 24 hours, nitrite concentration of medium was determined using Griess reaction to estimate the NO producing effect of ACA1 activating RAW264.7 macrophage, it shows in FIG. 14. After RAW 264.7 macrophage activated by ACA1, it can stimulate macrophage producing NO at 20 μg/ml, and the yield of nitrite is 13.2 μM; the yields of nitrite are 16.2 μM and 17.8 μM at 160 μg/ml (FIG. 14). It shows that ACA1 can activate RAW264.7 macrophage directly to promote it producing NO.

Figure 15:
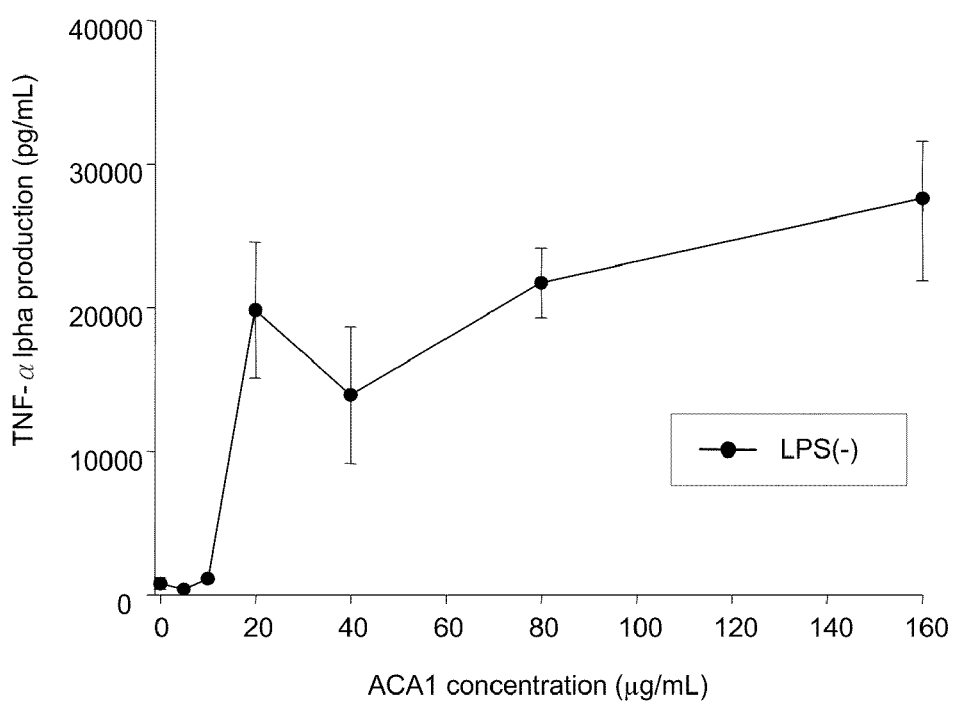
FIG. 15 shows the effect of ACA1 in activating RAW 264.7 macrophage to produce TNF-alpha.

(b) After ACA1 and RAW264.7 macrophage were co-cultivated for 24 hours, TNF-alpha concentration of the medium was determined using ELISA to estimate the activating effect of ACA1 on RAW264.7 macrophage in producing TNF-alpha. The result is shown in FIG. 15. After RAW 264.7 macrophage activated by ACA1, it can stimulate macrophage producing TNF-alpha at 20 μg/ml, and the yield of TNF-alpha is 2000 pg/ml, the more ACA1 concentration produce, the more TNF-alpha yield produce (FIG. 15). It shows that ACA1 can activate RAW264.7 macrophage directly to promote it secreting TNF-alpha.

Figure 16:
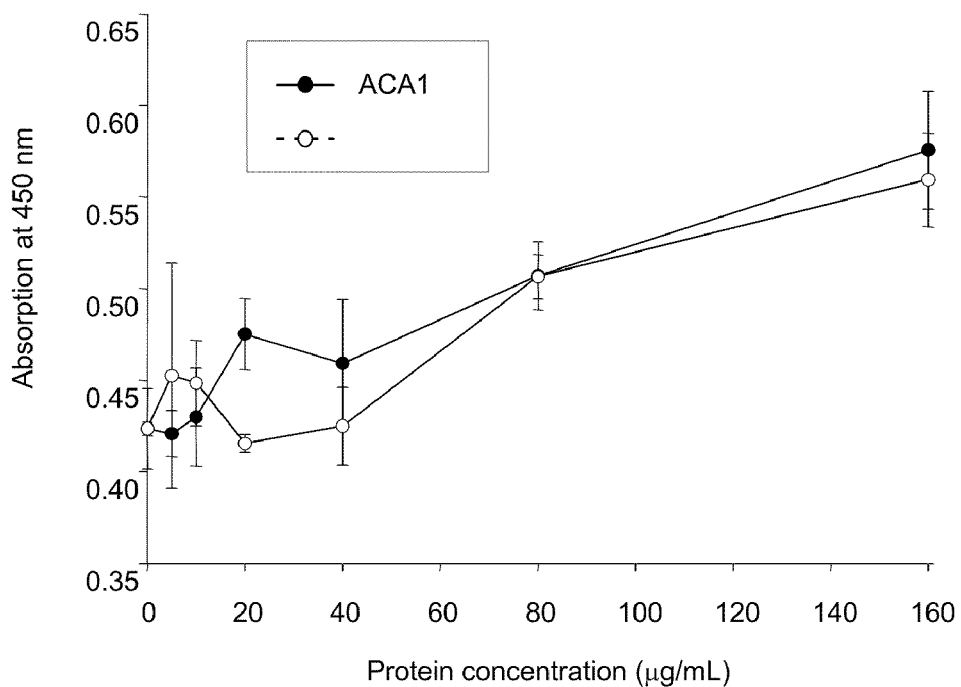
FIG. 16 shows the effect of ACA1 in increasing the efficiency of mouse spleen cell in ingesting BrdU to promote cell proliferation.

5. ACA1 activates mouse spleen cell (a) After ACA1 and mouse spleen cell were co-cultivated for 72 hours, the proliferation of mouse spleen cell is determined using BrdU Assay. BrdU Assay is uridine replaced by BrdU. To make divided cell ingesting BrdU, when cell proliferate and divide, and to recognize the BrdU uptake for cell by the BrdU specific antibody, therefore BrdU can be determined by antibody, herewith to infer the cell proliferation. As shown in FIG. 16, the more ACA1 concentration is, the more mouse spleen cell proliferate, it can stimulate cell proliferation and increases BrdU ingestion of mouse spleen cell at the concentration of ACA1 up to 20 μg/ml (FIG. 16). Therefore, ACA1 can activate mouse spleen cell to stimulate mouse spleen cell proliferation.

Figure 17:
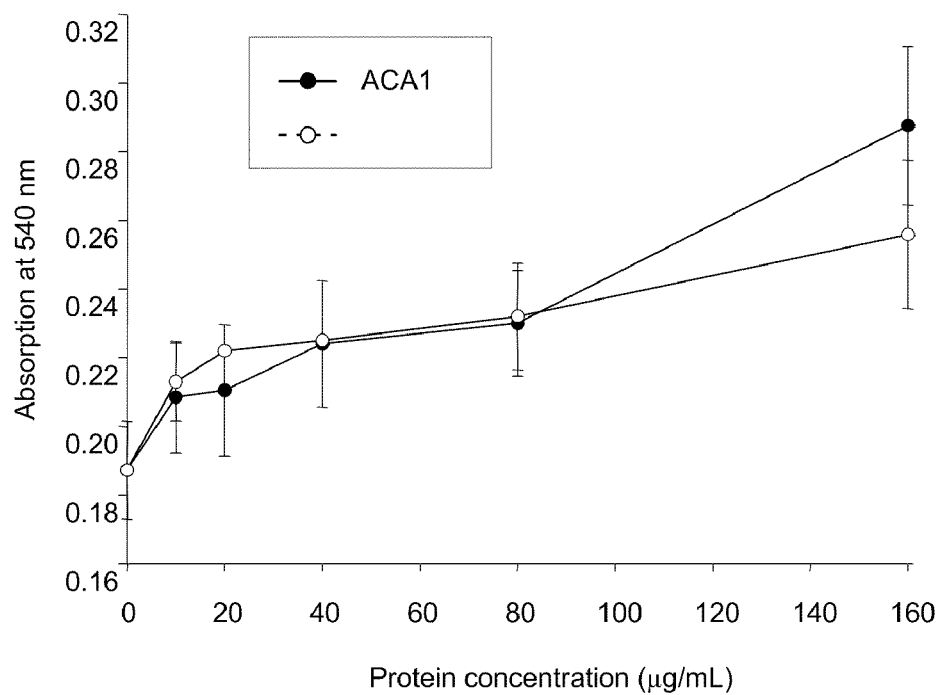
FIG. 17 shows the effect of ACA1 in increasing the efficiency of mouse spleen cell in metabolizing MTT to promote cell proliferation.

(b) After ACA1 and mouse spleen cell were co-cultivated for 72 hours, the metabolic activity of mouse spleen cell was determined using MTT Assay to estimate the proliferation effect of mouse spleen cell. MTT Assay transform MTT tetrazolium salt to blue, orange formazan using enzyme, this reaction works in live cell, and formazan producing in the cell transfer to medium by DMSO, it has direct proportion between formazan producing and the number of live cell. It can be the target of cell survival rate or proliferation rate, due to the ability of cell reducing MTT represents mitochondrion activity. The result of MTT Assay is shown in FIG. 17 ACA1 can stimulate cell proliferation at 10 μg/ml and up (FIG. 17). Therefore, ACA1 can activate mouse spleen cell to stimulate mouse spleen cell proliferation.

Figure 18:
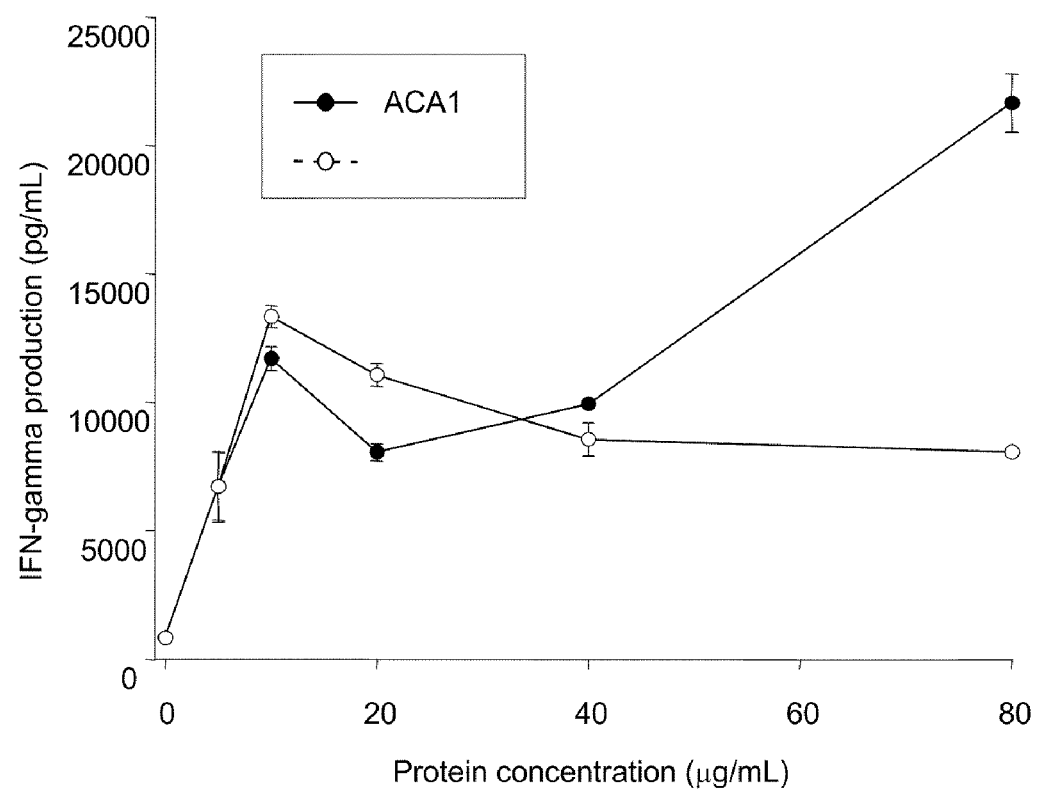
FIG. 18 shows the effect of ACA1 in irritating mouse spleen cell to secrete IFN-gamma.

(c) After co-cultivate ACA1 and mouse spleen cell for 72 hours, determine IFN-gamma concentration of medium by ELISA, the result shows the IFN-gamma secretion is 21653 pg/ml at 80 μg/ml ACA1 (FIG. 18). Therefore, ACA1 can activate mouse spleen cell to promote mouse spleen cell secreting IFN-gamma.

The present invention will be described through the following examples.

EXAMPLE 1

ACA1 Purification

1. Cultivation of *Antrodia camphorata* Mycelium

The *Antrodia camphorata* strain is BCRC 35396 (purchased from Food Industry Research and Development Institute).

Plate Culture: The medium used is MEA (malt extract agar) purchased from Difco, USA, which contains malt extract 20 g/L, glucose 20 g/L, peptone 1 g/L and agar 20 g/L. After it is autoclaved, the medium is allowed to cool to 65° C., then poured to a plate directly. The medium on the plate is inoculated with *Antrodia camphorata* mycelium, and then cultivated at 25° C. Red mycelium can be observed growing after 2 weeks.

Broth Culture: The broth used is MEA (malt extract agar) purchased from Difco, USA, which contains malt extract 20 g/L, glucose 20 g/L, peptone 1 g/L and agar 20 g/L. Cut 8 blocks, 0.25 cm² each, the plate medium growing *Antrodia camphorata* mycelium, and inoculate them in a 200-ml flask containing 100 ml of broth. Cultivate it by oscillation at 25° C. and 100 rpm for 3 weeks, then do the following.

2. Purification of ACA1 from *Antrodia camphorata* Mycelium

The step of ACA1 purification includes ammonium sulphate deposition, isolation, ion-exchange chromatography, etc., all carried out at 4° C.

(a) The ferment and mycelium in *Antrodia* camphorataferment are separated by centrifugation at 8,000 g in a Sorvall-Kendro RC5C rotor for 30 min. After deposition, the mycelium is washed 3 times using R.O. water, then extra water is removed from the *Antrodia camphorata* ferment by centrifugation at 8000 g for 30 min. Put the mycelium into an extraction buffer (0.1%(v/v) β-mercaptoethanol in 5%(v/v) glacial acetic acid), grind it to a thick liquid using 1.0 mm glass bead in a BEAD-BEATER cell disruption machine (at 4° C., for 5 times, 3 min/time spaced by 5 min). The resultant thick liquid is centrifuged at 12,000 g for 30 min.

(b) Ammonium sulphate was slowly added to the superstrata of the thick liquid to 95% saturation and the mixture was stirred overnight. It is then centrifuged at 18,000 g for 1 hour. The precipitates were dialysed against 5 liters of 10 mM Tris-HCl buffer, pH 8.2 for 120 h with daily changes of the dialysis solution. The protein dialysate was centrifuged at 18,000 g for 10 min, and the superstrata was collected as crude protein liquid of *Antrodia camphorata* ammonium sulphate.

(c) The crude protein liquid of *Antrodia camphorata* ammonium sulphate was pured in a DEAE-52 cellulose column (Whatman, DE-52), which was pre-equilibrated with 10 mM Tris-HCl, pH 8.2. The column was first washed with a buffer, then eluted with a linear gradient of NaCl (0-0.5 M) in the same buffer to wash off the protein. The effluent from the column is collected by a fractionator, and its absorbance at 280 nm was measured, yielding several protein peaks. The liquids collected from different collecting areas were subjected to SDS-PAGE analysis using 12% polyacrylamide slab gel.

(d) The protein obtained from the isolation step was purified by Akta fast protein liquid chromatography (FPLC) of Amersham Biosciences. According to the anion absorption characteristic of the isolated protein, Mono-Q column from Amersham Biosciences was chosen for purification. The Mono-Q column was pre-equilibrated with 10 mM Tris-HCl buffer, pH 8.2. After the sample was input, the column was eluted with a linear gradient of NaCl (0-0.5 M) in same buffer to wash off the protein on the wall. The effluent from the column was collected by a fractionator, and its adsorbance at 280 nm was measured, yielding several protein peaks. The liquid obtained from different collecting areas were subjected to SDS-PAGE analysis using 12% polyacrylamide slab gel.

EXAMPLE 2

SDS-Polyacrylamide Slab Gel Electrophoresis

1. Preparation of SDS-Polyacrylamide Slab Gel (a) Plate gel apparatus: Electrophoresis is performed on a Bio-Rad MiniProtein3 gel apparatus. The plate gel electrophoresis apparatus comprises two pieces of plan glass placed upright, each of which is fixed at both sides of glass by clips so that the gel can be held in between.

(b) Preparation of 12% polyacrylamide slab separating gel: After 3 ml polyacrylamide (30% acrylamide and 0.8% N,N'-methylene-bis-acrylamide) was well mixed with 1.9 ml 1.5M Tris-HCl, pH 8.8 buffer and 0.1 ml 10% SDS, a vacuum pump was used to remove air bubbles. Then 50 µl freshly prepared APS, 5.5 µl TEMED and 2.5 ml distilled water were added. Said prepared gel solution was injected into said glass device. After the gel solidified, the step of making stacking gel was.

(c) Preparation of 3% polyacrylamide slab stacking gel: After 0.5 ml polyacrylamide (30% acrylamide and 0.8% N,N'-methylene-bis-acrylamide) was well mixed with 0.76 ml 1.5M Tris-HCl, pH 6.8 buffer and 30 µl 10% SDS, a vacuum pump was used to remove the air bubbles. The 30 µl freshly prepared APS, 3.4 µl TEMED and 1.76 ml distilled water were added. Said prepared gel solution was injected on said solidified separating gel, and a comb was put on it. A U shaped jar for holding protein samples would be formed after the gel solidified.

2. Tank Buffer Preparation 14.4 g glycine and 10 ml 10% SDS solution were added into 3 g Tris-base, then distilled water was added to 1000 ml to make a 0.1% SDS, 25 mM Tris-glycine buffer, pH 8.3.

3. Protein Sample Preparation

100 µl of 1 mg/ml *Antrodia camphorata* protein solution was added with 10 µl 10% SDS solution, 5 µl β-mercaptoethanol, 2 µl 1.5M Tris-HCl, pH 8.8 buffer, a drop of glycerol and 2 µl 0.05% bromophenol blue. The mixture was heated at 100° C. for 10 min. Its molecular mass is compared by using LMW marker standard protein including phosphorylase b (97 kDa), bovine serum albumin (67 kDa), ovalumin (43 kDa), carbonic anhydrase (30 kDa), soybean trypsin inhibitor (20.1 kDa), and lactalbumin (14.4 kDa).

4. Operation of Gel Electrophoresis

To Fixd the plate on the device of gel electrophoresis, put the concave glass toward to electrophoresis bath, and then take off the comb to be U type jar on the plate. The electrophoresis bath fills with tray buffer. 30 µl protein sample has injected into U type jar of gel and connect the electrode. 50 V current passes through first until bromophenol blue moving to border between separating gel and stacking gel, and then changes the current to 100 V. When the indicator moves to the site which is apart 1 cm from the bottom of plate, it stops the electrophoresis, and picks up the separating gel and puts the gel on the dish for staining and distaining.

5. Staining and Destaining (a) Staining solution preparation: Dissolve 1.25 g Coomassie Brilliant Blue in 227 ml methanol and 46 ml acetic acid, then add distilled water to 500 ml. After thorough mixing, the solution is filtered.

(b) Destaining solution preparation: Mix 50 ml acetic acid with 75 ml methanol, and add distilled water to 1000 ml.

(c) The plate gel after gel electrophoresis: To immerse the plate gel into staining solution for 30 min, then pour out said solution, and change the solution to distaining solution. After to change distaining solution several times, the protein sites of gel show the blue color.

EXAMPLE 3

Periodic Acid-Schiff Stain

After SDS-PAGE analysis, the gel immerses into TCA solution to fix 30 min, rinse the gel several times and immerse the gel into periodic acid-acetic acid [1% periodic acid (w/v) and 3% acetic acid (w/w)] for 60 min, rinse the gel 3 times by distilled water, 10 min per time, and then immerse the gel into Schiff reagent, keep away from light, at 4° C., 50 min. After the gel displayed the color, rinse the gel with distaining solution (10% acetic acid) several times to distain the background color, and then rinse it with distilled water several times, and then preserve it in 50% methanol or in aridity.

EXAMPLE 4

Ion Focusing Electrophoresis

Determine by using LKB PhastSystem, Amersham Biosciences, homogeneous 7.5% gel plate, it injects 60 μl deionized water into the middle of said plate, and pick up the plastics plate by tweezers. The gel puts into the plate by 45° angle to avoid the bubble producing, and makes the gel facing the red frame. 5 μl sample has drawed on the parafilm, put the sample onto frame by comb, and start to electrophoresis.
The condition of electrophoresis:
SAMPLE APPL. DOWN AT 1.20 Vh;
SAMPLE APPL. UP AT 1.30 Vh;
Step 1: 250 V, 10.0 mA, 3.0W, 15° C., 1 Vh;
Step 2: 250 V, 10.0 mA, 3.0W, 15° C., 1 Vh;
Step 3: 250 V, 10.0 mA, 3.0W, 15° C., 60 Vh.
Silver stain and distain the gel after electrophoresis, and then preserve the gel in aridity. The gel compared with Pharmacia pI calibration kit (pI 3-10) with positive control (OVA: pI 5.2).

EXAMPLE 5

Gel Filtration Analysis

According to the theorem of size exclusion, using gel filtration divides standard protein and ACA1 held up in column in order to determine molecular mass.
Material: gel filtration column Amersham Superdex 75 10/300; eluent buffer: 50 mM phosphate buffer, 0.15 M NaCl, pH 7.0; sample: sample filtrated by 0.2 μm filter first; protein standards: Amersham Molecular size standards for gel filtration of protein (Ribonuclease A, 13.7 kDa; Chymotrypsinogen A, 25 kDa; Ovalbumin, 45 kDa; Albumin, 66 kDa).
Chromatography: Gel filtration proceed by Amersham Akta FPLC system, 0.7 mL/min flow rate, it determines the hold up time of each standard protein and sample and flow volume. Making each Ve values of each peak to calculate the molecular mass.
Calculation: To calculate all Kav value of protein standard and sample by formula $Kav=(Ve-Vo)/(Vt-Vo)$, on above formula, Ve is flow volume of said protein, Vo is the volume that no held up on the column completely, Vt is total column volume. Drawing the standard curve, the Kav of protein standard is the vertical axle; the log (MW) of protein standard is the cross axle, and then to draw the slope and intercept of curve. Comparing Kav value of sample with standard curve calculate its molecular mass.
Practice said embodiment to get an immune regulating protein ACA1 of Antrodia camphorata, molecular mass 29 kDa, pI 5.3, and performs glycoprotein stain of the electrophoresis film to know that ACA1 is glycoprotein.

EXAMPLE 6

Hemagglutination Activity Analysis

Add 200 μl blood of health Balb/C mouse with PBS, and low speed centrifugal 3 times, and then dilute to 1.5% (v/v) blood with PBS. Put 0.1 ml sample protein into 96 well microplate. To elute with a linear gradient of PBS 0.5, 0.25, 0.125, 0.063, 0.0031 mg/ml, and well mixes 50 μl 1.5% (v/v) blood, and put it down for 2 hr. to observe hemagglutination activity by naked eye. The hemagglutination activity is explaining in hemagglutination titer: the definition of hemagglutination activity is observing the lowest concentration of protein when hemagglutination. Use this step to perform ACA1 analysis, it shows ACA1 do not have hemagglutination activity.

EXAMPLE 7

Amino Acid Sequence Analysis

To analyze FIP-aca sample purity of FPLC Mono Q column purification by SDS-PAGE gel electrophoresis, transfer to PVDF film and be coomassie blue staining, then analyze the sequence by ABI amino acid sequencer using the theorem of Edman reaction. According to HPLC atlas of amino acid residue, it figures out the N-terminal amino acid sequence of protein, After analyzes the sequence to know that the N-terminal sequence of ACA1 is

VNVTYDPFFDNPPNNLLYYAASSDDTN.

EXAMPLE 8

Test of Irritating Macrophage to Produce NO

According to the method disclosed for Sheu F., et al., J. Agric. Food Chem., 2001, 49: 1767-1772, after macrophage RAW 264.7 irritated by lipopolysaccharide, LPS, the macrophage displays a large number of NO synthesize enzyme, and arginine will be catalyzed to nitric oxide (NO), it combines with the NO produced from citrulline and activated oxide to form the NO free radical which has stronger offensive. NO free radical is the important weapon of macrophage to kill pathogenic bacteria. It usually determines the concentration of nitrite in cell medium to show the No concentration, wherein determining No product is an important target to assess the activity level of macrophage.
(a) RAW 264.7 macrophages cultivate in 96 well plate ($10^5$ cells/well), 5% $CO_2$ incubator, at 37° C., 24 hr, then 0, 5, 10, 20, 40, 80 and 160 μg/ml ACA1 added into well and cultivate in 5% $CO_2$ incubator, at 37° C., 20 hr.
(b) 100 μl cell culture adds 100 μl Griess reagent (0.05% N-(1-napthyl)ethyl-enediamine hydrochloride, 0.5% sulfanilamide, 2.5% orthophosphoric acid), in acidity solution, the nitrous acid of culture react with Griess reagent to become purple azo dye, it has the most absorbance at 540 nm. The nitrite concentration of sample is determined the absorbance of 540 nm via Bio-Rad Model 3550-UV ELISA Reader and calculated nitrite standard curve.
It shows after RAW 264.7 macrophage activated from ACA1, in the concentration of 20 μg/ml, it has the ability to stimulate macrophage producing NO, and the nitrite yield is 13.2 μM; in the concentration of 60 μg/ml, the nitrite yield is 16.2 μM and 17.8 μM (FIG. 15). The result shows that ACA1 can activate RAW 264.7 macrophage directly, and promotes macrophage producing NO.

EXAMPLE 9

TNF-Alpha Determination

Use TNF-alpha OptEIA Set, BD Pharmingen to quantitative analyze TNF-alpha of mouse spleen cell.
RAW 264.7 macrophages cultivate in 96 well plate ($10^5$ cells/well), 5% $CO_2$ incubator, at 37° C., 24 hr, then 0, 5, 10, 20, 40, 80 and 160 µg/ml ACA1 added into well and cultivate in 5% $CO_2$ incubator, at 37° C., 20 hr.

Reagents: (a) capture antibody: Anti-mouse TNF-alpha antibody;
(b) Detection antibody: Biotinylated anti-mouse TNF-alpha antibody;
(c) Enzyme Reagent: Avidin-horseradish peroxidase conjugate;
(d) Blocking buffer: PBS with 10% FBS;
(e) Assay diluent: PBS with 10% FBS;
(f) Wash buffer: PBS with 0.05% Tween 20.

Coating capture antibody injects into 96-well ELISA plate. After added 100 µl capture antibody in each well, the plate is overnight at 4° C. Next day, wash the plate 3 times with wash buffer. Added the blocking buffer into ELISA plate to decrease non-specific interference, after it incubates at 37° C., 1 hr, wash the plate 3 times with wash buffer. Added 100 µl cell culture into ELISA plate for incubate at 37° C., 1 hr, then wash the plate 3 times with wash buffer. Added 100 µl detection antibody and enzyme reagent (avidin-HRP into ELISA plate for incubate at 37° C., 1 hr, then display the color by ABTS, and determine the absorbance of 405 nm by Bio-Rad Model 3550-UV ELISA Reader, Bio-Rad. Every experiment repeats 3 times and compares with standard curve to determine sample concentration for calculating its yield.

It shows after RAW 264.7 macrophage activated from ACA1, in the concentration of 20 µg/ml, it has the ability to stimulate macrophage producing TNF-alpha, and the TNF-alpha yield is 20000 pg/ml; the more ACA1 concentration is, the more TNF-alpha yield produces (FIG. 17). The result shows that ACA1 can activate RAW 264.7 macrophage directly, and promotes macrophage producing TNF-alpha.

EXAMPLE 10

BrdU Ingest Analysis

Mouse spleen cell isolation: After Balb/C mouse was coma by ether, and makes the mouse cervical dislocation to take out spleen cell of mouse. Spleen grinded by sand site of slide and put it in medium with 10 ml DMEM, centrifugal with 1,600 rpm, 10 min, room temperature. After removing upper liquid, use 1 ml RBC lysis buffer to rinse cell then add 9 ml PBS, centrifugal with 1,600 rpm, 5 min. After removing upper liquid and put it in medium with 10 ml DMEM to rinse cell and makes cell well mixed.

Use Roche BrdU cell proliferation for analysis, according to Vista D. T., et al., 1991, Cancer research, 51: 2515-2520, and all P. A. et al., 1990, J. Pathol., 162:285-294, BrdU assay utilizes the characteristic of cell proliferation need DNA replication because of DNA replication is an important factor of cell proliferation. DNA replication is the way using to determine cell mitosis and cell proliferation. BrdU (5-bromo-2'-deoxyuridine) has replaced thymidine to combine with DNA, after combination, BrdU uptaked by antibody recognition cell which is specific to BrdU. Therefore, BrdU can be determined by antibody in immune analysis, herewith it can infers the activation of cell proliferation.

Reagents: (a) BrdU solution: To add 20 µl BrdU into 2 ml culture medium to be 100 µM BrdU;
(b) Anti-Brud-POD: To add 100 µl stock solution into 10 ml antibody dilution solution. To add Anti-BrdU-POD powder into 1.1 ml deionized water, and mix 10 min to be stock solution;
(c) Washing solution: To add 10 ml of 10 times concentration washing solution into 90 ml deionized water;
(d) Stop solution (1M $H_2SO_4$): 18.78 M $H_2SO_4$ dilutes to 18.78 times to be 1M $H_2SO_4$.

Cultivate isolated lymphocyte into DMEM medium, and modulate the cell number to $5 \times 10^6$ cells/ml. Seed the cell culture into 96 well plate ($5 \times 10^5$ cells/well), and add 0, 10, 20, 40, 80, 160 and 320 µg/ml ACA1 in to well, the ConA (1 µg/ml) be the control, and cultivate in 5% $CO_2$ incubator, at 37° C., 48 hr.

To add 10 µl BrdU in to each well, and cultivate in same situation for 4 hr, and remove the culture medium, wash cell using washing solution, and then dry the plate. Add 200 µl fix denat solution into each well, and stay in room temperature for 30 min, then wash the well, it adds 100 µl Anti-BrdU-POD, and stays it in room temperature for 30 min, then adds 100 µl chromogenic stock, and stays it in room temperature for 10 to 30 min, and determine the absorbance of 450 nm by Bio-Rad Model 3550-UV ELISA Reader, Bio-Rad.

It shows the more ACA1 concentration is, the more cell proliferation of mouse spleen cell produce. Therefore, ACA1 can activate mouse spleen cell and irritate the cell proliferation of mouse spleen cell.

EXAMPLE 11

MTT Assay

According to Marshall N. J., et al., 1995, Growth regul., 5:69-84, MTT assay is the method to analysis cell proliferation, with XTT assay co-named micoculture tetrazolium assay (MTAs), it can analyzes the characteristic of cell life, growth, and disunite. MTT assay is a fast chromogenic, and it uses in immunology initially. It uses enzyme to transform the MTT tetrazolium salt [3-(4,5 dimethylthiazol-2-yl-2,5-diphenyl tetrazolium bromide to blue product MTT formazan. MTT transform in live cell and it accumulates in cell. After MTT dissolved by DMSO, it can determines the absorbance of 540 nm and quantitatively determine. It has direct ratio between Formazan yield and its amount. The ability of cell reducing MTT shows the activity of mitochondrion, therefore, it can be the target of cell survival rate. It usually used to determine cell survival rate and the phagecytosis of macrophage, due to MTT is quick, economy and no radioelement pollution. To compare cell survival rate determined by MTT chromogenic with merger of radioactivity nucleic acid, it shows it has 0.8 relations between them.

According to the method disclosed for Sheu F., et al., J. Agric. Food Chem., 2001, 49: 1767-1772.

(a) Isolated lymphocyte cultivate in DEME medium and the medium seeds in 96 well plate ($10^5$ cells/well), then 0, 10, 20, 40, 80, 160 and 320 µg/ml ACA1 added into well and the ConA (1 µg/ml) be the control, and both cultivate in 5% $CO_2$ incubator, at 37° C., 48 hr.

(b) To add 20 µl MTT in to each well, and cultivate in same situation for 5 hr, then centrifugal, remove medium, add DMSO, and stay for 5 min. To determined the absorbance of 540 nm via Bio-Rad Model 3550-UV ELISA Reader.

(c) The cell proliferation shows as the absorbance of control (ConA treatment).

After mouse spleen cell co-cultivates with ACA1 for 72 hr, determine the cell metabolism activity of mouse spleen cell to estimate the proliferation of mouse spleen cell. The result of MTT assay in FIG. 18 shows that it can stimulate cell proliferation at the ACA1 concentration more than 10 µl/ml (FIG.

18). Therefore, ACA1 can activate mouse spleen cell and stimulate proliferation of mouse spleen cell.

EXAMPLE 12

IFN-Gamma Determination

Quantitative analysis of IFN-gamma of T-lymph was performed using IFN-gamma OptEIA Set provided by BD Pharmingen.

Reagents: (a) capture antibody: Anti-mouse IFN-gamma antibody;
  (b) Detection Antibody: Biotinylated anti-mouse IFN-gamma antibody;
  (c) Enzyme Reagent: Avidin-horseradish peroxidase conjugate;
  (d) Blocking buffer: PBS with 10% FBS;
  (e) Assay diluent: PBS with 10% FBS;
  (f) Wash buffer: PBS with 0.05% Tween 20.

Mouse Spleen Cell Isolation:
  (a) After Balb/C mouse was coma by ether, and makes the mouse cervical dislocation to take out spleen cell of mouse. Spleen grinded by sand site of slide and put it in medium with 10 ml DMEM, centrifugal with 1,600 rpm, 10 min, room temperature. After removing upper liquid, use 1 ml RBC lysis buffer to rinse cell then add 9 ml PBS, centrifugal with 1,600 rpm, 5 min. After removing upper liquid and put it in medium with 10 ml DMEM to rinse cell and makes cell well mixed.
  (b) To get mouse spleen cell, and modulate the cell number to $5\times10^6$ cells/ml, and ACA1 added in cell to incubate for 48 hr then collect the cell medium.
  (c) Coating capture antibody injects into 96-well ELISA plate. After added 100 μl capture antibody in each well, the plate is overnight at 4° C. Next day, wash the plate 3 times with wash buffer. The blocking buffer has added into ELISA plate to decrease non-specific interference, after incubate at 37° C., 1 hr, wash the plate 3 times with wash buffer. 100 μl cell culture has added into ELISA plate for incubate at 37° C., 1 hr, then wash the plate 3 times with wash buffer. 100 μl detection antibody and enzyme reagent (avidin-HRP) added into ELISA plate for incubate at 37° C., 1 hr, then it displays the color by ABTS, and determines the absorbance of 405 nm by Bio-Rad Model 3550-UV ELISA Reader, Bio-Rad. Every experiment repeats 3 times and compares with standard curve to determine sample concentration for calculating its yield.

After mouse spleen cell was co-cultivated with ACA1 for 72 hr, the concentration of IFN-gamma in the medium was determined by ELISA. The result shows that when ACA1 is 80 μg/ml, the secrete value of IFN-gamma is 21,653 pg/ml, therefore. It shows that ACA1 can activate mouse spleen cell to enhance its production of IFN-gamma.

Practicing said embodiment yields a protein ACA1 of *Antrodia camphorata* having the following amino acid sequence or having amino acid sequence more than 90% similar to the following amino acid sequence:

VNVTYDPFFD-NPNNSLSYVA-CSDGTNGLLT-KGYTTLGSLP-DFPYIG

GAYA-IAGWNSPSCG-TCWELTYNNV-SINILGIDTA-AGFNIALTAM-

NVLTNNAAVD-LGEVDAAAIQ-VDSSVCGL,

ACA1 possesses immunomodulatory activity. It can be used as additive in foods and drinks, or it can be used with an excipient and other chemicals for biomedical purposes.

Although the invention has been explained in relation to its preferred embodiment, it is to be understood that many other possible modifications and variations can be made without departing from the spirit and scope of the invention as hereinafter claimed.

---

We claim:

1. An isolated *Antrodia camphorata* protein ACA1 having the amino acid sequence as set forth in SEQ ID NO: 2.

2. An *Antrodia camphorata* protein ACA1 of claim 1, said protein further possessing immunomodulatory activity in stimulating macrophage cells.

3. A chemical composition comprising as active ingredient an *Antrodia camphorata* protein ACA1 of claim 1, said chemical composition having immunomodulatory activity in stimulating macrophage cells.

* * * * *

UNITED STATES PATENT AND TRADEMARK OFFICE
CERTIFICATE OF CORRECTION

PATENT NO. : 7,531,627 B2  Page 1 of 1
APPLICATION NO. : 11/015078
DATED : May 12, 2009
INVENTOR(S) : Sheu et al.

It is certified that error appears in the above-identified patent and that said Letters Patent is hereby corrected as shown below:

In the title page, item (12), "She et al." should read --Sheu et al.--.

In the title page, item (75), the first Inventor's name "Fuu She" should read --Fuu Sheu--.

Signed and Sealed this

Fifteenth Day of June, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 354
<212> TYPE: DNA
<213> ORGANISM: Antrodia camphorata
<220> FEATURE:
<221> NAME/KEY: CDS
<222> LOCATION: 1..354

<400> SEQUENCE: 1 gtt aac gtg acc tat gac cct ttt ttt gac aac cca aac aac tct         45
Val Asn Val Thr Tyr Asp Pro Phe Phe Asp Asn Pro Asn Asn Ser
 1               5                  10                  15 ctc agc tac gtc gct tgc tcg gat ggt acc aat ggt ctt ctc acc         90
Leu Ser Tyr Val Ala Cys Ser Asp Gly Thr Asn Gly Leu Leu Thr
            20                  25                  30 aaa ggg tat acc acc ttg ggc tcc ctc cct gat ttc cct tac att        135
Lys Gly Tyr Thr Thr Leu Gly Ser Leu Pro Asp Phe Pro Tyr Ile
        35                  40                  45 gga ggc gca tat gcc atc gca gga tgg aat tcc ccg agc tgt ggc        180
Gly Gly Ala Tyr Ala Ile Ala Gly Trp Asn Ser Pro Ser Cys Gly
    50                  55                  60 aca tgt tgg gag cta aca tac aac aac gtc agc atc aac ata ttg        225
Thr Cys Trp Glu Leu Thr Tyr Asn Asn Val Ser Ile Asn Ile Leu
65                  70                  75
```

-continued

```
ggg atc gac aca gct gcg ggc ttc aac att gca ctt acg gct atg      270
Gly Ile Asp Thr Ala Ala Gly Phe Asn Ile Ala Leu Thr Ala Met
            80                  85                  90 aac gta ctc acc aat aac gcg gcc gta gat ctg ggg gag gtt gat      315
Asn Val Leu Thr Asn Asn Ala Ala Val Asp Leu Gly Glu Val Asp
            95                  100                 105 gca gcg gca ata cag gtc gac tcg tcc gtg tgc ggg ctg              354
Ala Ala Ala Ile Gln Val Asp Ser Ser Val Cys Gly Leu
            110                 115         118
```

<210> SEQ ID NO 2
<211> LENGTH: 118
<212> TYPE: PRT
<213> ORGANISM: Antrodia camphorata

<400> SEQUENCE: 2

```
Val Asn Val Thr Tyr Asp Pro Phe Phe Asp Asn Pro Asn Asn Ser
 1               5                  10                  15

Leu Ser Tyr Val Ala Cys Ser Asp Gly Thr Asn Gly Leu Leu Thr
                20                  25                  30

Lys Gly Tyr Thr Thr Leu Gly Ser Leu Pro Asp Phe Pro Tyr Ile
                35                  40                  45

Gly Gly Ala Tyr Ala Ile Ala Gly Trp Asn Ser Pro Ser Cys Gly
                50                  55                  60

Thr Cys Trp Glu Leu Thr Tyr Asn Asn Val Ser Ile Asn Ile Leu
                65                  70                  75

Gly Ile Asp Thr Ala Ala Gly Phe Asn Ile Ala Leu Thr Ala Met
                80                  85                  90

Asn Val Leu Thr Asn Asn Ala Ala Val Asp Leu Gly Glu Val Asp
                95                  100                 105

Ala Ala Ala Ile Gln Val Asp Ser Ser Val Cys Gly Leu
                110                 115         118
```